Aug. 23, 1960 H. S. CRAWFORD Plant Pat. 1,968
BARBERRY PLANT
Filed Nov. 5, 1959
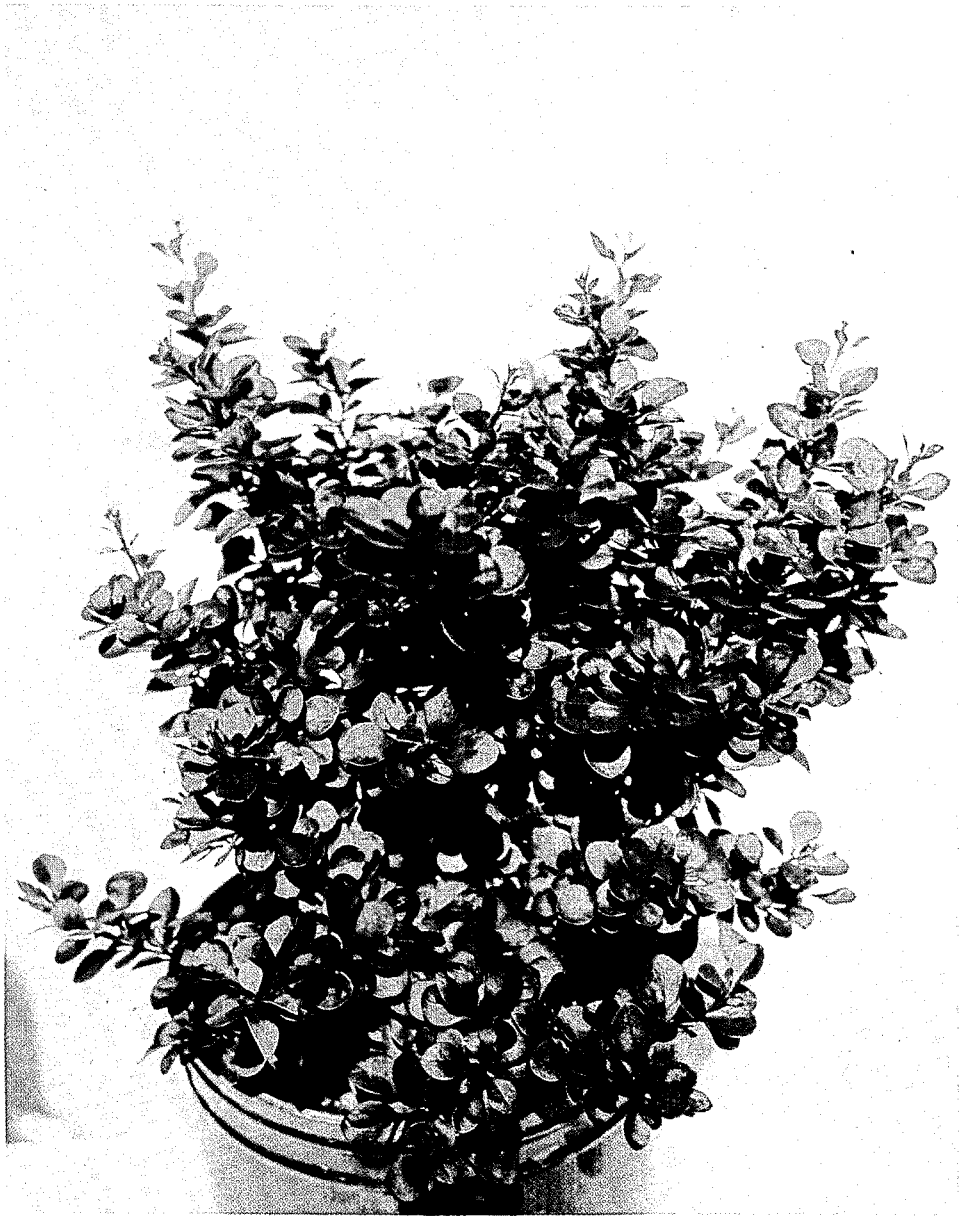
INVENTOR
H. S. Crawford
BY Robb & Robb
ATTORNEYS United States Patent Office Plant Pat. 1,968
Patented Aug. 23, 1960

1,968

BARBERRY PLANT

Harold S. Crawford, Ottawa, Kans., assignor to The Willis Nursery Company, Ottawa, Kans., a partnership Filed Nov. 5, 1959, Ser. No. 851,206

1 Claim. (Cl. 47—59)

The present invention relates to a new and distinct variety of barberry plant which was discovered by me on cultivated property in my nursery at Ottawa, Kansas, in which I hold a partnership interest, as indicated in the assignment recorded of even date with the filing of this application, said discovery occurring as a newly found seedling.

At the time of my initial discovery of this seedling, I was engaged in the growing of a block of some 10,000 two-year old field grown plants derived from two-year old seedlings of *Berberis thunbergi atropurpurea*. My attention was attracted to one particular plant amongst these plantings because of its outstanding Brilliant Red color, symmetry of form, dense habit of growth, and uniformity of foliage. Accordingly, I took steps to carefully preserve this plant and keep it under close observation, and subsequently, I asexually reproduced the same from softwood cuttings which I set out in my nursery aforesaid.

Continued observations of the original seedling, as well as the asexually reproduced plants, fully confirmed that the same is a new and distinct variety, and definitely distinguished from all other varieties, as evidenced by the following unique combination of characteristics which are outstanding therein, and which have been found come true to form and transmissible by asexual propagation:

(1) Uniform and symmetrical growth habit;
(2) Relatively large, round and dense foliage; and
(3) A distinctive Brilliant Red foliage color.

The accompanying drawing shows a typical specimen plant of my new barberry variety, with the foliage in different stages of development and as depicted in color as nearly true as it is reasonably possible to make the same in a color illustration of this character.

The following is a detailed description of the new variety, with color terminology in accordance with Nickerson's Color Fan, published by Munsell Color Company Incorporated of Baltimore, Maryland, except where general color terms of ordinary dictionary significance are obvious, and based upon specimens grown outdoors at Ottawa, Kansas:

Parentage: Newly found seedling of *Berberis thunbergi atropurpurea*.

Propagation: Holds its distinguishing characteristics through succeeding propagations by softwood cuttings.

*Plant*

Growth: Medium size; spreading; dense; hardy.

Wood: Smooth.

*New wood.*—Color—Moderate Red, Color 2.5 R 4/10.

*Mature wood (2 year).*—Color—Moderate Yellowish Brown, Color 10 YR 4/4, streaked with Dark Red, Color 2.5 R 3/7.

Foliage:

*Quantity.*—Many; arranged to present a whorl-like appearance.

*Size.*—Large. Length—from ½" to 1". Width—from ¼" to 1".

*Shape.*—Ovate, with rounded apiculated apex and narrowing at base.

*Thickness.*—From thin to medium.

*Color.*—New foliage—Moderate Red, Color 2.5 R 4/10. Mature foliage—Dark Red, Color 2.5 R 3/7.

*Margin.*—Smooth.

*Petiole.*—Short.

*Glands.*—None.

*Stipules.*—None.

Spines: Varying from simple to 3-parted; average length from ¼ to ⅜".

Flowers: None produced or observed to date.

Fruit: None produced or observed to date.

I claim:

A new and distinct variety of barberry plant of the *Berberis thunbergi atropurpurea* type, substantially as herein shown and described, characterized particularly as to novelty by the unique combination of a uniform and symmetrical habit of growth, relatively large, round and dense foliage, and a distinctive Brilliant Red general color tonality of the foliage.

No references cited.